US00PP34486P2

(12) United States Plant Patent
Ammerlaan

(10) Patent No.: US PP34,486 P2
(45) Date of Patent: Aug. 9, 2022

(54) *ECHEVERIA* PLANT NAMED 'OVPEARLS13'

(50) Latin Name: *Echeveria gibbiflora*
Varietal Denomination: OVPEARLS13

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 17/803,287

(22) Filed: Apr. 21, 2022

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP29,758 P3 * 10/2018 Ammerlaan ..... A01H 5/12
Plt./373

OTHER PUBLICATIONS

Ovata website citation for *Echeveria* 'indigo pearl'. https://www.ovata.nl/en/supure-assortment/indigo-pearl/. 3 pages.*

* cited by examiner

*Primary Examiner* — Karen M Redden
(74) *Attorney, Agent, or Firm* — Samuel R. McCoy, Jr.

(57) ABSTRACT

A new and distinct variety of *Echeveria* plant named 'OVPEARLS13' which is characterized by a small basal rosette of loosely held, broadly obovate foliage with a relaxed attitude, lightly to moderately glaucous juvenile foliage that is somewhat glossy, moderately glaucous mature foliage with a matte luster, and foliage that is covered with a layer of greyed-green epicuticular wax which gives the foliage a greyed-green appearance. The new variety has shown to be uniform and stable in the resulting generations from asexual propagation.

4 Drawing Sheets

Latin name of the genus and species: The Latin name of the genus and species of the novel variety disclosed herein is *Echeveria gibbiflora.*

Variety denomination: The inventive variety of *Echeveria* disclosed herein has been given the variety denomination 'OVPEARLS13'.

BACKGROUND OF THE INVENTION

Parentage: 'OVPEARLS13' originated as a naturally occurring, whole-plant mutation *Echeveria gibbiflora* 'Green Pearl' (Community Plant Variety Rights grant number 30762). The inventor of 'OVPEARLS13' is a commercial ornamental plant producer and regularly discovers mutations of *Echeveria* sp. at his greenhouse operation in Bleiswijk, The Netherlands. For said mutations which seem to exhibit commercial potential, cuttings are taken to produce trial plants which are subsequently grown for evaluation.

The variety now called 'OVPEARLS13' was initially discovered in early 2018 as a whole-plant mutation of *Echeveria gibbiflora* 'Green Pearl' which exhibited somewhat glossy juvenile foliage, slightly darker green foliage which remained green year-round and was devoid of the pink coloration along the margins. At the time of discovery, cuttings were taken and the resulting plants were evaluated at the inventor's greenhouse. After further evaluation it was determined that the candidate plant's unique foliage characteristics would prove favorable for commercial marketability. The new plant was given the denomination 'OVPEARLS13'.

Asexual Reproduction: Asexual reproduction of the new cultivar 'OVPEARLS13', by way of rooting leaf cuttings, was first initiated in the autumn of 2017 at the inventor's commercial greenhouse in Bleiswijk, the Netherlands. Through eleven subsequent generations, the unique features of this cultivar have proven to be stable and true to type.

SUMMARY OF THE INVENTION

The cultivar 'OVPEARLS13' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS13'. These characteristics in combination distinguish 'OVPEARLS13' as a new and distinct *Echeveria* cultivar:

1. 'OVPEARLS13' exhibits a small basal rosette of loosely held foliage; and
2. 'OVPEARLS13' exhibits broadly obovate foliage with a relaxed attitude; and
3. 'OVPEARLS13' exhibits lightly to moderately glaucous juvenile foliage that is somewhat glossy; and
4. 'OVPEARLS13' exhibits moderately glaucous mature foliage with a matte luster; and
5. 'OVPEARLS13' exhibits yellow-green to green foliage that is covered with a layer of greyed-green epicuticular wax which gives the foliage a greyed-green appearance.

BOTANICAL DESCRIPTION OF THE PLANT

Figure 1:
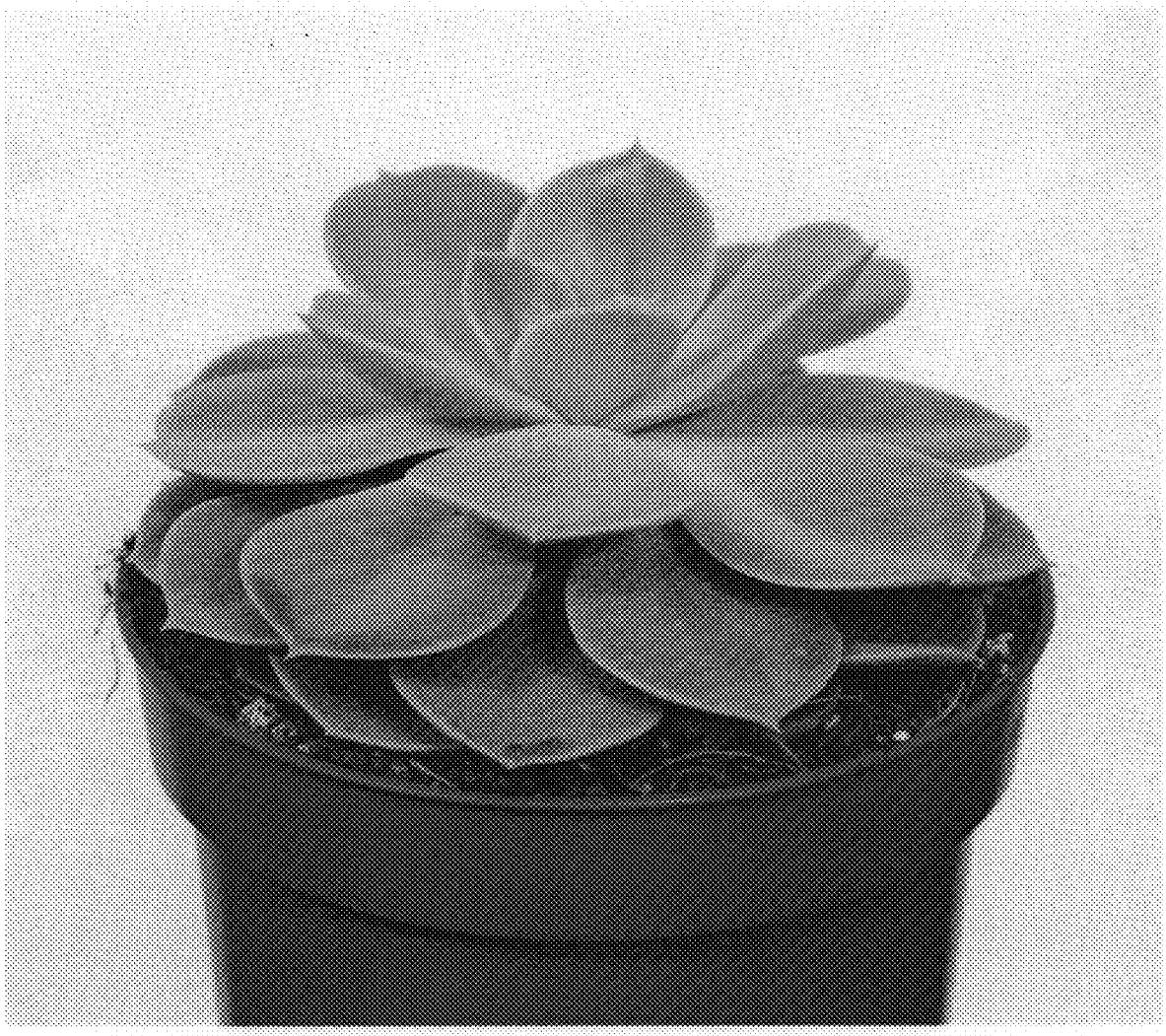
FIG. 1 illustrates, as nearly true as it is reasonably possible to make the same in color photographs of this type, an exemplary plant of 'OVPEARLS13' grown in a commercial greenhouse in Bleiswijk, the Netherlands. This plant is approximately 8 months old, shown planted in a 12 cm container.
Figure 2:
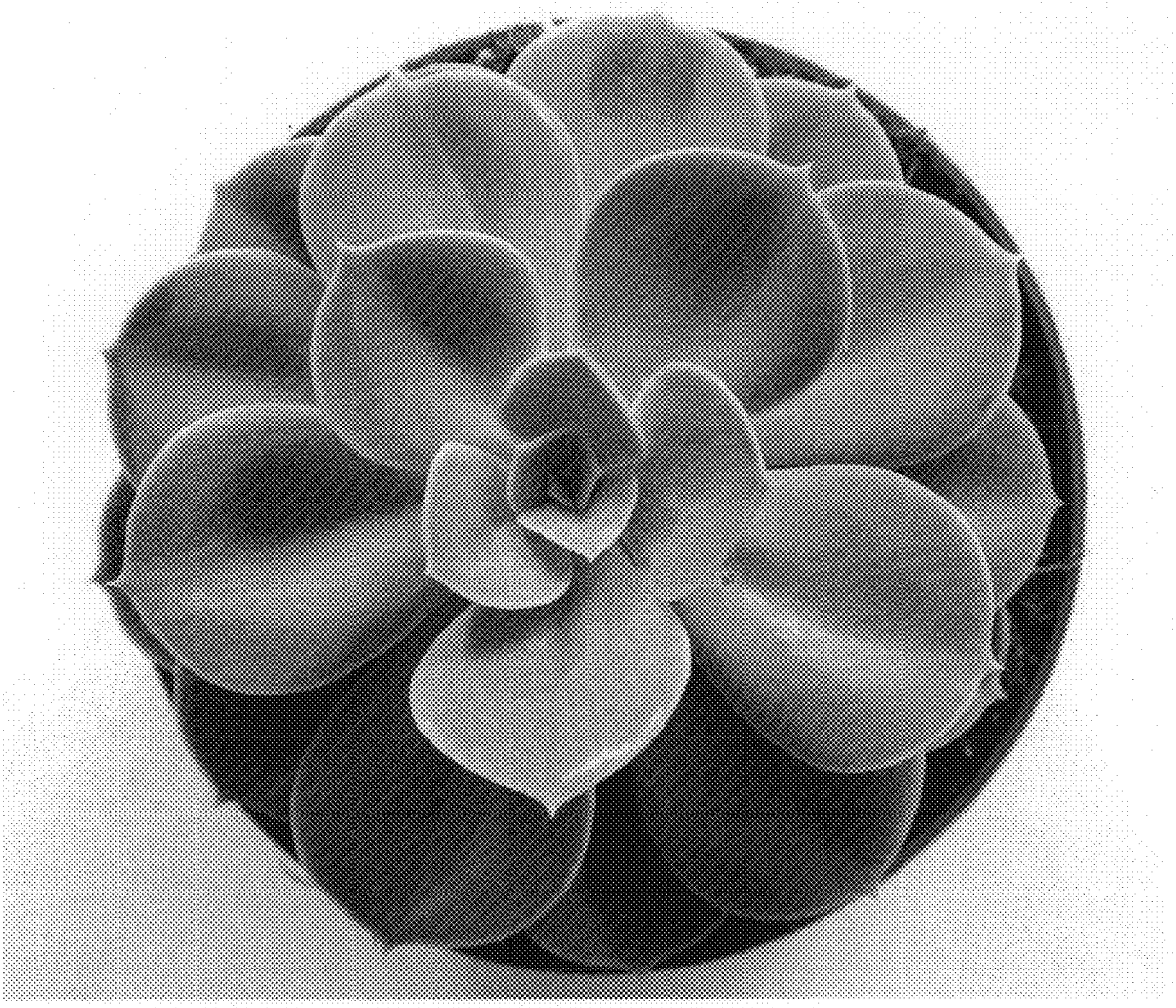
FIG. 2 illustrates, as nearly true as it is reasonably possible to make the same in color photographs of this type, the typical foliage arrangement of 'OVPEARLS13'.
Figure 3:
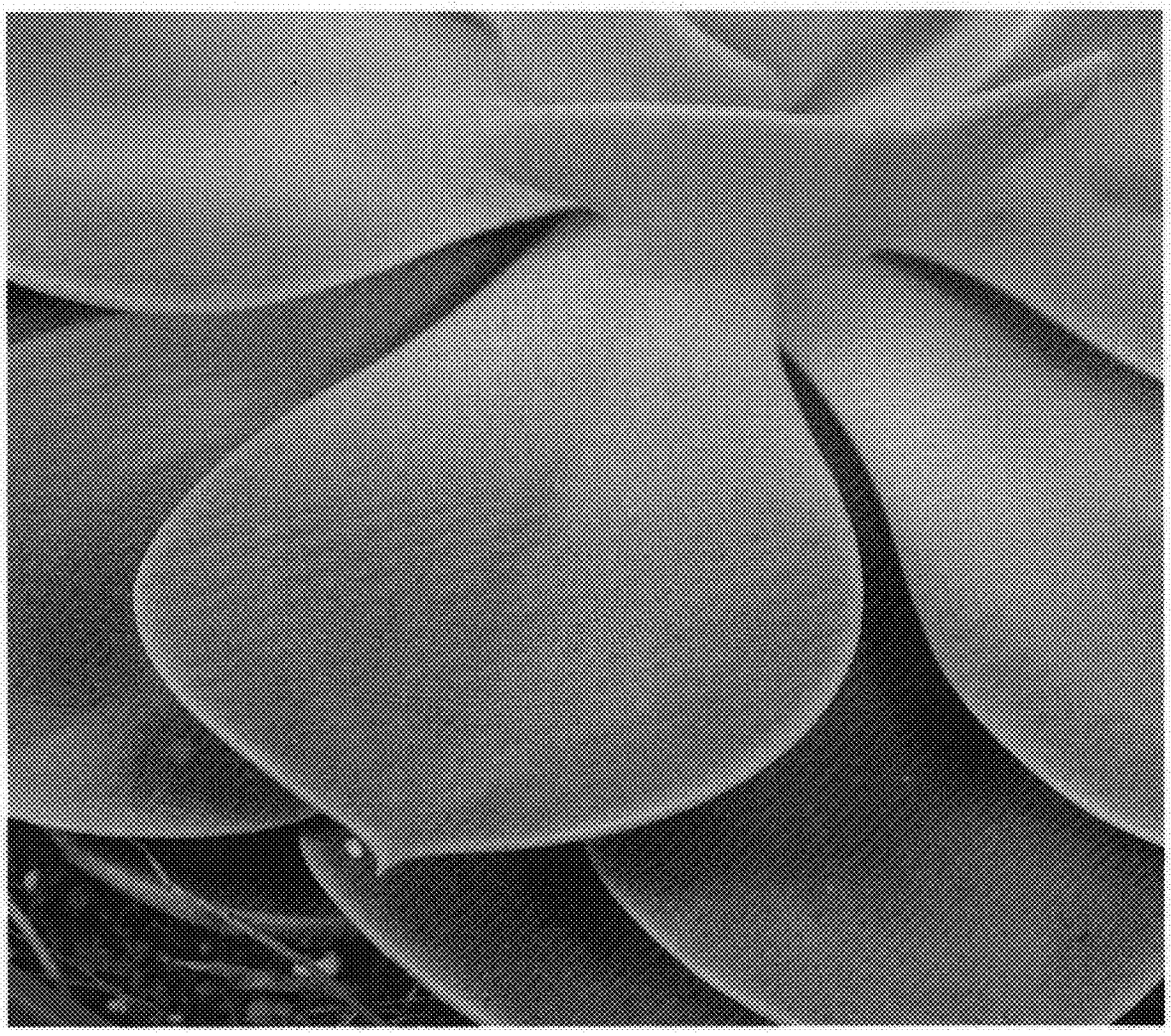
FIG. 3 illustrates, as nearly true as it is reasonably possible to make the same in color photographs of this type, the adaxial surface of the mature foliage 'OVPEARLS13'.
Figure 4:
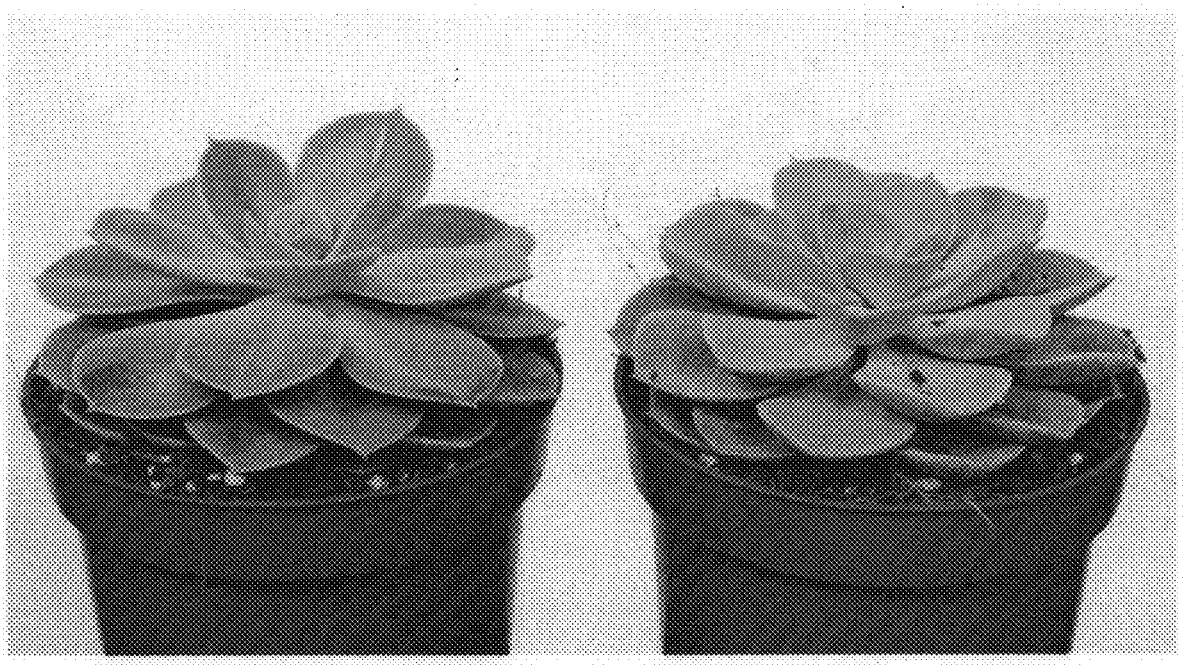
FIG. 4 illustrates, as nearly true as it is reasonably possible to make the same in color photographs of this type, a comparison between 'OVPEARLS13', left, and its parent, 'Green Pearl, on the right.

The following observations and measurements made in December of 2021 describe averages from a sample set of six specimens of 8-month-old 'OVPEARLS13' plants grown in 12 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS13' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'OVPEARLS13' and a comparison with the parent plant and closest known comparator is provided below.

Plant description:

*Growth habit.*—Succulent perennial with foliage growing in a compact, non-branched basal rosette, eventually forms a short stem with age.

*Plant form.*—Flattened globular to flattened.

*Height from soil level to top of foliar plane.*—6.1 cm.

*Plant spread.*—Average of 12.0 cm.

*Growth rate.*—Somewhat slow-growing.

*Plant vigor.*—Moderately vigorous.

*Propagation.*—Type — Leaf cuttings. Time to initiate rooting — Approximately 5 weeks at an approximate temperature of 21 degrees Celsius. Crop time — Approximately 1 year to produce a marketable plant in a 7 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 36 leaves per rosette.

*Shape.*—Broad obovate.

*Dimensions.*—5.5 cm long, 3.3 cm wide, and 0.6 cm thick, on average.

*Aspect.*—Very slightly concave.

*Attitude.*—Juvenile foliage at the center of the rosette exhibits an upright and outward attitude; foliage becomes progressively more relaxed as it matures and becomes nearly horizontal to slightly pendulous at the outer whorls of the rosette.

*Apex.*—Apiculate.

*Base.*—Cuneate.

*Margin.*—Entire with no undulation.

*Pubescence, texture and luster of the adaxial surface.*—Glabrous, smooth, moderately glaucous and matte; juvenile foliage which is lightly to moderately glaucous and somewhat glossy.

*Pubescence, texture and luster of the abaxial surface.*—Glabrous, smooth, and matte; moderately glaucous.

*Color.*—Juvenile foliage, adaxial surface — Green, nearest to RHS 138A; fading to yellow-green towards the base, nearest to a mixture of RHS 146C and 146D; narrowly margined yellow-green, nearest to RHS 147D. Leaves are covered with a thin layer of epicuticular wax which is colored greyed-green, nearest to RHS 189B. Juvenile foliage, abaxial surface — Green, nearest to RHS 138A; fading to yellow-green towards the base, nearest to RHS 147D; narrowly margined yellow-green, nearest to RHS 147D. Leaves are covered with a thin layer of epicuticular wax which is colored greyed-green, nearest to RHS 189B. Mature foliage, adaxial surface — Nearest to a mixture of green and yellow-green, RHS NN137C and 147B; fading to yellow-green towards the base, nearest to in between RHS 147C and 147D; narrowly margined yellow-green, nearest to RHS 147D. Leaves are covered with a thin layer of epicuticular wax which is colored greyed-green, nearest to RHS 189B. Mature foliage, abaxial surface — Yellow-green, nearest to RHS 147B; fading to a lighter shade of yellow-green towards the base, nearest to RHS 148C; narrowly margined yellow-green, nearest to RHS 147D. Leaves are covered with a thin layer of epicuticular wax which is colored greyed-green, nearest to RHS 189B.

*Venation.*—Pattern — No venation is visible. Color, adaxial surface — No venation is visible. Color, abaxial surface — No venation is visible.

*Petiole.*—No petiole; leaves are sessile.

Inflorescence: No flowering has been observed to date.

Comparisons with the parent plant: Plants of the new cultivar 'OVPEARLS13' differ from the seed parent, *Echeveria gibbiflora* 'Green Pearl' (Community Plant Variety Rights grant number 30762) in the following characteristics described in Table 1 below.

TABLE 1

| Characteristic | 'OVPEARLS13' | Green Pearl |
|---|---|---|
| Foliage size. | Larger than 'Green Pearl'. | Smaller than 'OVPEARLS13'. |
| Foliage aspect. | Very slightly concaved. | Concaved. |
| Glaucosity of the foliage. | Lighter than 'Green Pearl'. | Stronger than 'OVPEARLS13'. |
| General coloration of the foliage. | Remains green year-round. | Becomes suffused with red-purple at certain times of the year. |

Comparisons with the closest known comparator: Plants of the new cultivar 'OVPEARLS13' differ from *Echeveria lilacina* 'AMIECH2002' (U.S. patent application Ser. No. 17/300,670), which is the closest known comparator, in the following characteristics described in Table 2 below.

TABLE 2

| Characteristic | 'OVPEARLS13' | 'AMIECH2002' |
|---|---|---|
| Foliage attitude. | More relaxed than 'AMIECH2002'. | More upright than 'OVPEARLS13'. |
| Luster of the juvenile foliage. | Somewhat glossy. | Matte. |
| General coloration of the mature foliage. | Greyed-green; more towards grey, relative to 'AMIECH2002'. | Greyed-green; more towards green, relative to 'OVPEARLS13'. |
| General coloration of the foliar margins. | Lightly margined with greyed-purple. | Narrowly margined with a translucent greyed-green. |

That which is claimed is:

1. A new and distinct variety of *Echeveria gibbiflora* plant named 'OVPEARLS13', substantially as described and illustrated herein.

* * * * *